US012746305B2

(12) United States Patent
Yang et al.

(10) Patent No.: US 12,746,305 B2
(45) Date of Patent: Sep. 29, 2026

(54) PHOTOCURABLE HEMOSTATIC COMPOSITION

(71) Applicant: SNVIA CO., LTD., Busan (KR)

(72) Inventors: Seung Yun Yang, Miryang-si (KR); Hyeseon Lee, Miryang-si (KR); Keum-Yong Seong, Busan (KR); Samdae Park, Busan (KR); Kang Oh Lee, Busan (KR)

(73) Assignee: SNVIA CO., LTD., Busan (KR)

( * ) Notice: Subject to any disclaimer, the term of this patent is extended or adjusted under 35 U.S.C. 154(b) by 385 days.

(21) Appl. No.: 18/265,964

(22) PCT Filed: Nov. 15, 2021

(86) PCT No.: PCT/KR2021/016607
§ 371 (c)(1),
(2) Date: Jun. 7, 2023

(87) PCT Pub. No.: WO2022/124610
PCT Pub. Date: Jun. 16, 2022

(65) Prior Publication Data
US 2024/0050622 A1 Feb. 15, 2024

(30) Foreign Application Priority Data
Dec. 10, 2020 (KR) ........................ 10-2020-0172355

(51) Int. Cl.
*A61L 24/08* (2006.01)
*A61L 24/00* (2006.01)

(52) U.S. Cl.
CPC ........... *A61L 24/08* (2013.01); *A61L 24/0031* (2013.01); *A61L 2300/418* (2013.01); *A61L 2300/802* (2013.01); *A61L 2400/04* (2013.01)

(58) Field of Classification Search
CPC ................. A61L 24/08; A61L 24/0031; A61L 2300/802; A61L 2300/418; A61L 2400/04
See application file for complete search history.

(56) References Cited

U.S. PATENT DOCUMENTS

2013/0231474 A1 9/2013 Auzely et al.

FOREIGN PATENT DOCUMENTS

| | | | | |
|---|---|---|---|---|
| CN | 103724455 A | | 4/2014 | |
| WO | WO 9910019 | * | 3/1999 | ........... A61L 24/043 |
| WO | 2014-072330 A1 | | 5/2014 | |
| WO | WO 2019195324 | * | 10/2019 | ............ C09J 133/14 |

OTHER PUBLICATIONS

Chandrasekharan, A. et al., "In situ Photocrosslinkable Hyaluronic Acid-Based Surgical Glue with Tunable Mechanical Properties and High Adhesive Strength", Journal of polymer science part A: Polymer chemistry, 2019, vol. 57, No. 4, pp. 522-530.
Sani, E. S. et al., "Engineering adhesive and antimicrobial hyaluronic acid/elastin-like polypeptide hybrid hydrogels for tissue engineering applications", ACS biomaterials science & engineering, 2018, vol. 4, No. 7 , pp. 2528-2540.
Benjamin D. Fairbanks et al., "Photoinitiated polymerization of PEG-diacrylate with lithium phenyl-2,4,6-trimethylbenzoylphosphinate: polymerization rate and cytocompatibility", Biomaterials, vol. 30, Issue 35, Dec. 2009, pp. 6702-6707.

* cited by examiner

*Primary Examiner* — Shirley V Gembeh
(74) *Attorney, Agent, or Firm* — Revolution IP, PLLC

(57) ABSTRACT

The present invention relates to a photocurable hemostatic composition and, specifically, to a photocurable liquid hemostatic composition containing a hyaluronic acid-based photocrosslinkable compound and a photoinitiator as active ingredients, and to a hemostatic agent of a film or sponge formulation freeze-dried from the composition, wherein, by increasing the degree of substitution of a photocrosslinkable functional group, the composition can quickly form a gel or a film adhesive layer within a few seconds during light radiation, and the resulting gel remains in a body more stably for a long time, thus enhancing hemostasis and tissue regeneration effects.

4 Claims, 1 Drawing Sheet

PHOTOCURABLE HEMOSTATIC COMPOSITION

CROSS REFERENCE TO PRIOR APPLICATIONS

This application is a National Stage Application of PCT International Patent Application No. PCT/KR2021/016607 filed on Nov. 15, 2021, under 35 U.S.C. § 371, which claims priority to Korean Patent Application No. 10-2020-0172355 filed Dec. 10, 2020,respectively, which are all hereby incorporated by reference in their entirety.

TECHNICAL FIELD

The present disclosure relates to a photocurable hemostatic composition, specifically, a photocurable liquid hemostatic composition including a hyaluronic acid-based photocrosslinkable compound and a photoinitiator as active ingredients, and a hemostatic agent in a film or sponge formulation obtained by freeze-drying the composition.

BACKGROUND ART

Suppression of bleeding is one of the important stages in the treatment. When oxygen supply is dwindled due to excessive bleeding that brings a loss in more than 30% of the total blood, the organs in the body fail to function properly. Afterwards, when more than 40% of the blood is lost due to failure in hemostasis, it may lead to death due to hemorrhage-induced shock. Therefore, it is important to prevent emergencies due to excessive bleeding with appropriate hemostatic measures in the event of bleeding due to the mistake of medical staffs in situations such as open and endoscopic surgery, including injury caused by accidents.

For surgical procedures such as conventional sutures, it is hard to quickly cope with emergency, and thus tissue adhesives such as sealants and hemostatic agents are being actively researched to replace the same.

Major commercialized tissue adhesives include cyanoacrylate glue which is a type of instant adhesive and fibrin glue that mimics the blood clotting process. Cyanoacrylate is curable without a separate initiator and has high adhesiveness, but it loses adhesiveness and flexibility under a wet environment due to bleeding. Moreover, toxic by-products such as formaldehyde are produced during the decomposition process of cyanoacrylate, thus showing low biocompatibility.

Fibrin-based adhesives that mimic the coagulation reaction of blood (a crosslinking reaction of thrombin and fibrinogen) have hemostatic capability, but the coagulation reaction takes a long time, such that there is a limitation in the use for immediate hemostasis in emergency situations. In addition, there is a risk of infection by pathogens when extracted from human serum, and the use of heterologous proteins derived from animals may cause immune rejection.

Recently, attempts have been made to introduce photocrosslinkable groups into biopolymers such as gelatin for quick adhesion and hemostasis at the desired tissue. However, since the gelatin-based biopolymer has a low proportion of lysine that enables intramolecular introduction of the photocrosslinkable group, substitution takes place only in a limited range (10% or less) to require long-term light irradiation for hemostasis. In addition, gelatin is an animal-derived biopolymer, with a risk of immune response when used in the human body.

Therefore, it is necessary to develop a liquid hemostatic agent which overcomes the limitations of existing liquid hemostatic agents and has more effective hemostatic effects.

DISCLOSURE OF THE INVENTION

Technical Goals

An object of the present disclosure is to provide a liquid hemostatic composition using a biopolymer compound with excellent photocrosslinkability.

Another object of the present disclosure is to provide a hemostatic agent in a film formulation obtained by drying the liquid hemostatic composition.

Technical Solutions

In order to achieve the above object, the present disclosure provides a photocurable liquid hemostatic composition including a compound represented by the following Chemical Formula 1 or a pharmaceutically acceptable salt thereof; and a photoinitiator as active ingredients.

[Chemical Formula 1]

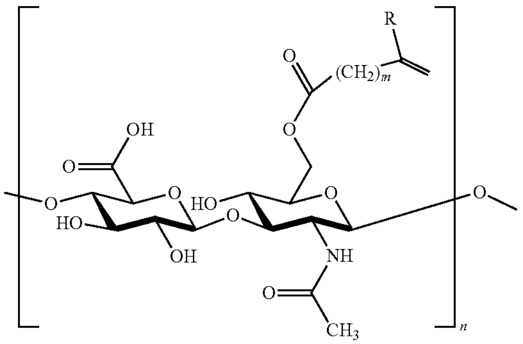

In the Chemical Formula 1, R may be hydrogen or C1-C4 alkyl, m may an integer from 0 to 10, and n may be an integer from 1 to 50000.

In addition, the present disclosure provides a hemostatic agent in a film or sponge formulation obtained by freeze-drying the photocurable liquid hemostatic composition.

Advantageous Effects

According to a photocurable liquid hemostatic composition and a hemostatic agent in a film or sponge formulation prepared by freed-drying the composition according to in the present disclosure, unlike existing cases that a photocrosslinkable functional group such as a methacrylate group is bonded to an —NH group of hyaluronic acid, by conjugating the photocrosslinkable functional group to an —OH group of hyaluronic acid to substitute with more photocrosslinkable functional groups, it is possible to quickly form a gel or film adhesive layer within a few seconds upon light irradiation, thereby ensuring convenient manufacturing and high reproducibility.

A gel formed by light irradiation stays in the body more stably for a long time, thereby enhancing the hemostatic and tissue regenerating effects.

In addition, the composition has superior adhesiveness even in wet tissues due to bleeding and thus is applicable as more effective hemostatic agents in various tissue sites.

BEST MODE FOR CARRYING OUT THE INVENTION

Figure 1:
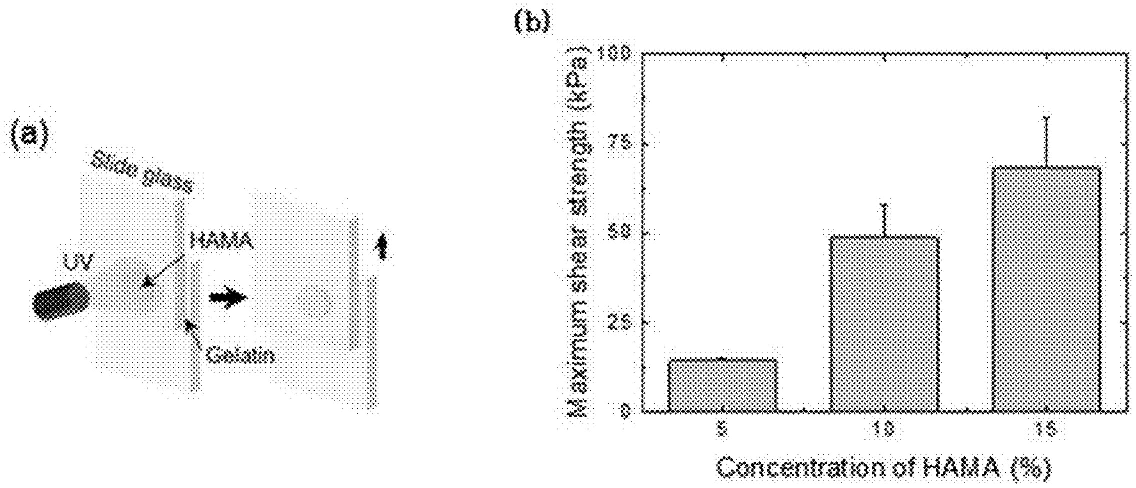
FIG. 1 relates to the adhesiveness of an HA-based hemostatic agent according to an example embodiment of the present disclosure, wherein (a) shows a method of measuring the adhesiveness of the hemostatic agent, and (b) shows a graph showing the adhesiveness according to concentration of the hemostatic agent.

Hereinafter, the present disclosure will be described in detail.

In order to overcome limitations of existing liquid hemostatic agents, the present inventor completed the present disclosure by introducing a photocrosslinkable functional group to hyaluronic acid (HA), a biopolymer that is aseptically producible, at a high substitution rate, and finding that excellent tissue adhesive and hemostatic effects were derived with immediate crosslinking in the form of a gel when irradiated with light in a specific wavelength.

The present disclosure provides a photocurable liquid hemostatic composition including a compound represented by the following Chemical Formula 1 or a pharmaceutically acceptable salt thereof; and a photoinitiator as active ingredients.

[Chemical Formula 1]

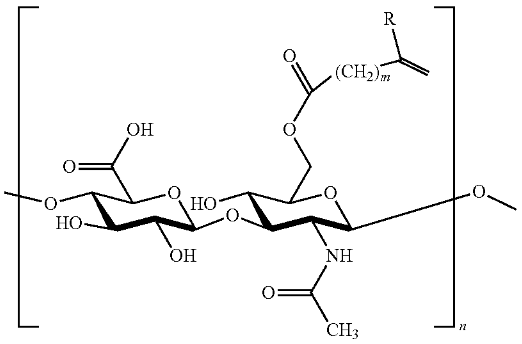

In the Chemical Formula 1, R may be hydrogen or C1-C4 alkyl, m may an integer from 0 to 10, and n may be an integer from 1 to 50000.

The compound or salt thereof may be one that a photocrosslinkable functional group is bonded to a hyaluronic acid repeating unit that has excellent biocompatibility.

Preferably, it may be hyaluronic acid methacrylate (HAMA) to which a methacrylate group is bonded.

The photocrosslinkable functional group may be selected from methacrylate, butylacrylate, and pentaacrylate that are photocrosslinkable, preferably methacrylate, but is not limited thereto.

The compound may be used in a form of pharmaceutically acceptable salts to the extent that the same efficacy is derived.

As used herein, the term "pharmaceutically acceptable" refers to a state without toxicity to cells or humans that are exposed to the composition.

The salt may include any one form of pharmaceutically acceptable base salts or acid salts.

The base salt may be used in any one form of organic base salts and inorganic base salts and selected from the group consisting of sodium salts, potassium salts, calcium salts, lithium salts, magnesium salts, cesium salts, aminium salts, ammonium salts, triethyl amine salts and pyridinium salts, but is not limited thereto.

For acid salts, acid addition salts that are formed by free acids are useful. Inorganic acids and organic acids may be used as free acids, hydrochloric acid, bromic acid, sulfuric acid, sulfurous acid, phosphoric acid, diphosphoric acid, and nitric acid may be used as the inorganic acids, and citric acid, acetic acid, maleic acid, malic acid, fumaric acid, gluconic acid, methanesulfonic acid, benzenesulfonic acid, camphorsulfonic acid, oxalic acid, malonic acid, glutaric acid, acetic acid, glycolic acid, succinic acid, tartaric acid, 4-toluenesulfonic acid, galacturonic acid, embonic acid, glutamic acid, citric acid, aspartic acid, and stearic acid may be used as the organic acids.

In addition, the compound according to the present disclosure may include not only pharmaceutically acceptable salts, but also all salts, hydrates and solvates that may be prepared by conventional methods. For example, the compound may be prepared by dissolving in a water-miscible organic solvent such as acetone, methanol, ethanol, or acetonitrile, adding an excess of organic bases or an aqueous base solution of an inorganic base, and then undergoing precipitation or crystallization. Alternatively, it may be prepared by evaporating solvents or excess base from the mixture to dry and obtain an addition salt or undergoing suction filtration using the precipitated salt.

For the compound or salt thereof, as the photocrosslinkable functional group is bonded to the —OH group on hyaluronic acid, a degree of substitution for the photocrosslinkable functional group may become higher than that of existing compounds bonded to the NH group of hyaluronic acid, while the substitution may be accomplished theoretically up to 400%, such that the increased degree of substitution for the photocrosslinkable functional group may facilitate gel formation and enhance stability in vivo and thus be utilized as a hemostatic agent ensuring excellent therapeutic effects.

Preferably, the compound or salt thereof may have a number average molecular weight of 500 to 5,000,000 Da (Dalton). In the above range, the photocrosslinked hemostatic agent may have excellent mechanical strength and flexibility to retain the hemostatic effect by maintaining adhesion even with various movements involved in the human body.

Preferably, the compound or salt thereof may have an average viscosity of 10 to 3,000 cP (centipoise). The viscosity increases in proportion to the increase in the content of the compound, and the liquid hemostatic agent having the viscosity in the above range has excellent formability and applicability, such that its shape is processible in a form required in the affected area while securing applicability.

Preferably, the compound or salt thereof may be contained in an amount of 0.1 to 20 parts by weight with respect to a total of 100 parts by weight of the liquid hemostatic agent.

According to an example embodiment of the present disclosure, it has been found that the adhesiveness thereof increases when the content of HAMA increases to 5, 10, and 15 parts by weight, such that it may be preferable as a hemostatic composition when the compound or salt thereof is included in the above range.

In the present disclosure, the photoinitiator may be a non-toxic material in vivo and selected from lithium phenyl-2,4,6-trimethylbenzoylphosphinate or 2-hydroxy-4'-(2-hydroxyethoxy)-2-methylpropiophenone, preferably lithium-phenyl-2,4,6-trimethylbenzoylphosphinate, but is not limited thereto.

The photoinitiator may be contained in an amount of 0.001 to 1.0 parts by weight with respect to a total of 100 parts by weight of the liquid hemostatic agent, preferably 0.1 to 0.01 parts by weight, but is not limited thereto.

In the present disclosure, the photocurable liquid hemostatic composition stanches blood as a gel is formed within 10 seconds after light irradiation, preferably within 5 seconds.

The light irradiation may include not only UV irradiation, but also light irradiation in other wavelengths, including visible light, using photoinitiators having different absorption wavelengths.

As used herein, the term "gel" refers to a solid swollen by absorbing or including a solvent, preferably a hydrogel formed by photocrosslinkage, but is not limited thereto.

The hydrogel is a highly hydrated material made of hydrophilic polymers that form an organized three-dimensional network in the crosslinking process to form a soft, porous structure, and in particular, the hydrogel formed by photocrosslinkage is soft with excellent fluidity.

The gel formed by light irradiation may be maintained in the body for 1 to 4 weeks. By staying in the body for a long time, it is possible to enhance the hemostatic and tissue regenerating effects.

In addition, the present disclosure provides a hemostatic agent in a film or sponge formulation obtained by freeze-drying the liquid hemostatic composition.

The hemostatic agent in the film or sponge formulation may be effectively used in a spot where a large area of perforation or bleeding takes place, the hemostatic agent having the formulation may also carry out crosslinking reactions by light irradiation, and a portion in contact with blood may be partially dissolved to induce higher adhesion and hemostatic effects.

In addition, by using the liquid hemostatic agent and the hemostatic agent in the film or sponge formulation simultaneously or sequentially, it is possible to enhance the hemostatic effect.

For example, it is possible to enhance the adhesive and hemostatic effect by attaching the hemostatic agent in the film or sponge formulation to the bleeding site and then applying the liquid hemostatic agent thereto.

The corresponding features may be substituted in the above-described parts.

MODES FOR CARRYING OUT THE INVENTION

Hereinafter, in order to help understanding of the present disclosure, example embodiments will be described in detail. However, the following example embodiments are only to illustrate contents of the present disclosure, and the scope of the present disclosure is not limited to the following example embodiments. An example embodiment of the present disclosure is provided for more complete explanation of the present disclosure to a person of average skill in the art.

<Preparation Example 1> Preparation of HA-Based Compound (HAMA)

Scheme 1 below shows a process of preparing a compound to be used as a hyaluronic acid-based hemostatic agent.

[Scheme 1]

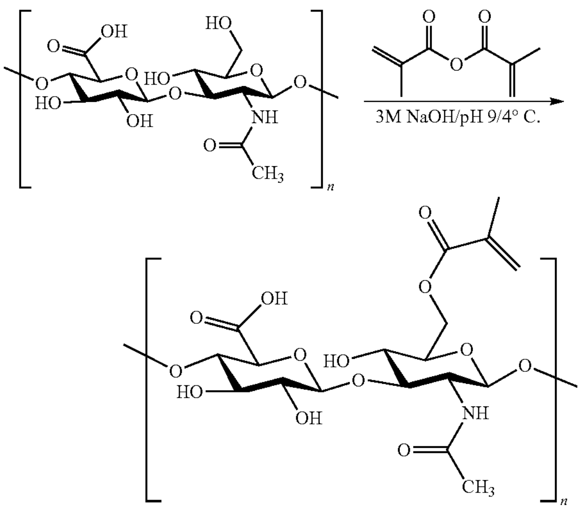

First, 10 g of hyaluronic acid (HA) (26 mmol) was added to 100 ml of water ($H_2O$) to prepare a first solution, and methacrylic anhydride (MA) and 3M NaOH were added to the first solution to prepare a second solution. Then, ethanol was added to the second solution to produce a precipitate, and the precipitate was purified and vacuum dried to prepare a compound (HAMA) on the right side of the Scheme above.

Yield: 85%, $^1$H-NMR (300 MHz, $D_2O$): δ(ppm)=5.9, 5.6, (2H, —C═$CH_2$), 4.5-4.3 (2H, $CH_2$), 3.8-3.0 (10H, CH), 1.7 (3H, $CH_3$), 1.8 (3H, $CH_3$).

<Example 1> Preparation of an HA-Based Hemostatic Agent and Adhesiveness Test The compound prepared in Preparation Example 1 was added by 5, 10, and 15% (w/v) compared to distilled water. A photoinitiator (lithium phenyl-2,4,6-trimethylbenzoylphosphinate) was added by 0.05% (w/v) compared to distilled water to prepare a HAMA hemostatic agent.

As shown in FIG. 1(*a*), 20% gelatin was applied and coated to the surface of a slide glass, then a hemostatic solution was applied over the coated gelatin layer, and UV was irradiated for 5 seconds to check adhesiveness.

As a result, as shown in FIG. 1(*b*), it was found that the adhesiveness of the HAMA adhesive increased with concentration.

Figure 2:
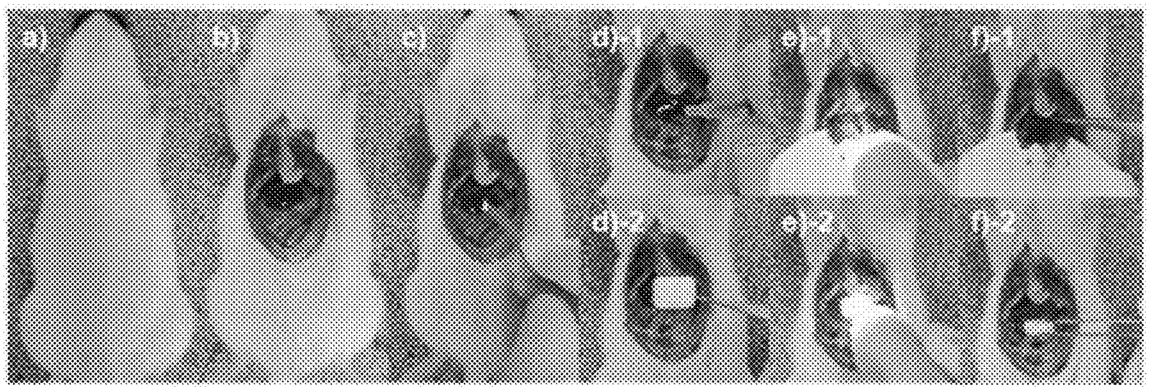
FIG. 2 shows a process for evaluating the hemostatic performance of an HA-based hemostatic agent according to another example embodiment of the present disclosure, wherein (a) shows an inhalation anesthesia process, (b) shows an incision process of the abdominal skin layer of anesthetized rats, (c) shows a process of forming a liver puncture using punch biopsy, (d)-1 shows a process of applying an HA-based liquid hemostatic agent, (d)-2 shows a process of applying an HA-based film hemostatic agent, (e)-1 and (e)-2 show processes of crosslinking the applied hemostatic agent (less than 5 seconds), and (f)-1 and (f)-2 show the appearance of perforation in which hemostasis is completed.

<Example 2> Evaluation on Hemostatic Performance of the HA-Based Hemostatic Agent Evaluation on the hemostatic performance of the HAMA hemostatic agent prepared according to Example 1 was verified through animal experiments using rats, as shown in FIG. 2.

First, an incision was made in the abdomen of the rat that had been anesthetized with isoflurane, a type of inhaled anesthetic for animals, and then the liver was artificially perforated using a punch biopsy. The perforated site was applied with HAMA liquid to hemostatic agent dissolved by 10 wt % (the degree of substitution: 150% or higher) or freeze-dried HAMA sponge-type film hemostatic agent, and then hemostasis took place by light irradiation within 5 seconds.

As a result, the HAMA based hemostatic agent had excellent adhesiveness even in wet tissues due to bleeding, and hemostasis took place through formation of a gel or film adhesive layer quickly within a few seconds (<less than 5 seconds). In addition, the formed gel was maintained stably for more than 3 weeks in vivo, and an effect of promoting treatment may be expected through the effect of supporting tissue regeneration.

Having described specific parts of the contents of the present disclosure in detail above, it is apparent for a person skilled in the art that such specific descriptions are merely a preferred example embodiment, and the scope of the present disclosure is not limited thereby. In other words, the substantive scope of the present disclosure is defined by the attached claims and their equivalents.

The invention claimed is:

1. A preparing method of sponge formulation for enhancing hemostatic and tissue regenerating effects in a subject in need of a hemostatic and tissue regenerating treatment, comprising:

preparing a photocurable liquid hemostatic composition comprising: a compound represented by the following Chemical Formula 1 or a pharmaceutically acceptable salt thereof; and a photoinitiator as active ingredients,

[Chemical Formula 1]

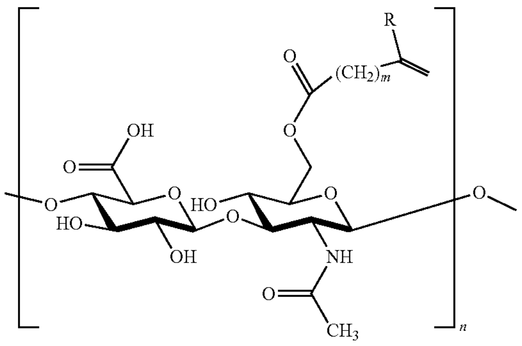

wherein in the Chemical Formula 1,

R is hydrogen or C1-C4 alkyl, m is an integer from 0 to 10, and n is an integer from 1 to 50000, wherein the compound or salt thereof is contained in an amount of 0.1 to 20 parts by weight with respect to a total of 100 parts by weight of a liquid hemostatic agent, wherein the photoinitiator is lithium phenyl-2,4,6-trimethylbenzoylphosphinate, is non-toxic, and is contained in an amount of 0.01 to 0.1 parts by weight with respect to a total of 100parts by weight of a liquid hemostatic agent; and freeze-drying the photocurable liquid hemostatic composition to obtain a sponge formulation, wherein the sponge formulation is capable of carrying out cross-linking reactions by light irradiation, wherein upon application to a bleeding site, a portion of the sponge formulation in contact with blood is partially dissolved to induce higher adhesion and hemostatic effects, and wherein upon light irradiation the sponge formulation forms a gel or film adhesive layer within 5 seconds to stanch bleeding, and the adhesive layer is maintained in the subject for 1 to 4weeks.

2. The preparing method of claim 1, wherein the compound or salt thereof has a number average molecular weight of 500 to 5,000,000 Da.

3. The preparing method of claim 1, wherein the compound or salt thereof has an average viscosity of 10 to 3,000 cP.

4. The preparing method of claim 1, wherein the compound or salt thereof is contained in an amount of 0.1 to 20 parts by weight with respect to a total of 100 parts by weight of a liquid hemostatic agent.

* * * * *